(12) United States Patent
Sirges et al.

(10) Patent No.: US 6,583,312 B2
(45) Date of Patent: Jun. 24, 2003

(54) PROCESS FOR PREPARING OPTICALLY ACTIVE TRIMETHYLLACTIC ACID AND ITS ESTERS

(75) Inventors: Wolfram Sirges, Düsseldorf (DE); Claus Dreisbach, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/864,906

(22) Filed: May 24, 2001

(65) Prior Publication Data

US 2002/0035271 A1 Mar. 21, 2002

(30) Foreign Application Priority Data

May 31, 2000 (DE) .......................................... 100 27 154

(51) Int. Cl.$^7$ ...................... C07C 69/675; C07D 27/24; C07D 307/02

(52) U.S. Cl. ..................... 560/179; 562/518; 562/579; 568/880; 568/881

(58) Field of Search ................................ 568/880, 881; 560/179; 562/518, 579

(56) References Cited

U.S. PATENT DOCUMENTS

| | | | |
|---|---|---|---|
| 4,556,740 A | 12/1985 | Hansen et al. | 568/13 |
| 4,691,037 A | 9/1987 | Yoshikawa et al. | 556/18 |
| 4,739,084 A | 4/1988 | Takaya et al. | 556/21 |
| 4,739,085 A | 4/1988 | Takaya et al. | 556/21 |
| 5,198,562 A | 3/1993 | Noyori et al. | 556/23 |
| 5,436,067 A | 7/1995 | Hanamoto et al. | 428/288 |
| 5,488,172 A | 1/1996 | Cereghetti et al. | 568/13 |
| 5,510,503 A | 4/1996 | Laue et al. | 556/21 |
| 5,710,339 A | 1/1998 | Laue et al. | 568/16 |
| 5,801,261 A | 9/1998 | Laue et al. | 556/16 |
| 6,284,925 B1 | 9/2001 | Knochel et al. | 564/415 |
| 6,348,620 B1 * | 2/2002 | Knochel et al. | 560/231 |

FOREIGN PATENT DOCUMENTS

| | | | |
|---|---|---|---|
| EP | 0 366 390 | 1/1994 | |
| EP | 0 901 997 | 3/1999 | |
| EP | 0 965 574 A2 * | 12/1999 | C07B/53/00 |

OTHER PUBLICATIONS

Bioorganic & Medicinal Chemistry Letters, vol. 5, 15, pp. 1729–1734, (month unavailable) 1995, α–Hydroxyamide Derived Aminodiols as Potent Inhibitors of HIV Protease, Saleem Ahmad, Aaila Ashfaq, Masud Alam, Gregory S. Bisacchi, Ping Chen, Peter T. W. Cheng, Jill A. Greytok, Mark A. Hermsmeier, Pin–Fang Lin, Karen A. Lis, Zoeb Merchant, Toomas Mitt, Mark Skoog, Steven H. Spergel, Joseph A. Tino, Gregory D. Vite, Richard J. Colonno, Robert Zahler and Joel C. Barrish.

Bull. Chem. Soc. JP., (month unavailable) 1968, 41 pp. 2178–2179, Syntheses of 3,3–Dimethyl–2–hydroxybutyric Acid and Tertiary Leucine and Their Optical Resolutions, Tadashi Tanabe, Shinichi Yajima and Masami Imaida.

Applied and Enviromental Microbiology, Mar. 1983, p. 884–891 vol. 45, No. 3, Microbial Resolution of α–Hydroxy Acids by Enantiospecifically Dehydrogenating Bacteria from Soil, Toyoaki Sawada, Mayumi Ogawa, Rieko Ninomiya, Kazuteru Yokose, Morio Fujiu, Kimihiro Watanabe, Yasuji Suhara and Hiromi B. Maruyama.

Chem. Ber. 124 pp. 849–859 (month unavailable) 1991, Synthese eines chiralen, nicht–racmischen Aziridions (α–Lactams)[1,2] Helmut Quast und Holger Leybach.

J. org. Chem. pp. 53, 1231–1238 (month unavailable)1988, Chiral Synthesis via Organoboranes. 15. Selective Reductions. 42. Asymmetric Reduction of Representative Prochiral Ketones with Potassium 9–O–(1,2:5, 6–Di–O–isopropylidene–α–D–glucofuranosyl)–9–boratabicyclo[3.3.1]–, Herbert C. Brown, Byung Tae Cho, and Won Suh Park.

J. Org. Chem. 51, pp. 3396–3398 (month unavailable) 1986, Asymmetric Reduction of α–Keto Esters with Potassium, 9–O–(1,2:5, 6–Di–O–isopropylidene–α–D–glucofuranosyl)–9–boratabicyclo[3.3.1]nonane. Chiral Synthesis of αHydroxy Esters with Optical Purity Approaching 100% ee, Herbert C. Brown et al.

Tetrahedron: Asymmetry vol. 5, No. 4, pp 675–690, (month unavailable) 1994, Enantioselective Hydrogenation Reactions with a Full Set of Preformed and Prepared in situ Chiral Diphosphine–Ruthenium (II) Catalysts. J.P. Genet, C. Pinel, V. Ratovelomanana–Vidal, S. Mallart, X. Pfister, L. Bischoff, M.C. Cano De Andrade, S. Darses, C. Galopin, J.A. Laffitte.

The Journal of Organic Chemistry, vol. 51, pp. 624–629 (month unavailable) 1986, Novel Construction of Penem Ring System from Penicillin Deravatives. Synthesis of 2–Carboxylpenem Derivative, Tetsuji Kametani, Naoaki Kanaya, Atsushi Nakayama, Tomoko Mochizuki, Shuichi Yokohama, and Toshio Honda.

Chem. Pharm. Bull. 39(4) pp. 1085–1087 (month unavailable) (1991), Synthesis of Axially Dissymmertric Biphenylbisphosphine Ligands, Bimiops and Asymmetric Hydrogenations of β–Keto Ester and α, β–Unsaturated Carboxylic Acid Catalyzed by their Ruthenium (II) Complexes[1], Naoko Yamamoto, Masanao Murata, Toshiaki Morimoto, and Kazuo Achiwa.

Synlett, Nov. 1991, pp. 827–829, Synthesis fo Atropisomeric Biphenylbisphosphine, 6,2'–Bis(diphenylphosphino)–3–methoxy–2, 4–dimethyl–4',6'–bis(trifluoromethyl)–1,1'–biphenyl (FUPMOP) and Its Use in Ruthenium (II)–Catalyzed Asymmetric Hydrogenation of a 3–Oxo Ester[1], Masanao Murata, Toshiaki Morimoto, Kazuo Achiwa.

(List continued on next page.)

Primary Examiner—Brian Davis
(74) Attorney, Agent, or Firm—Godfried R. Akorli; Richard E.L. Henderson

(57) ABSTRACT

The invention relates to a novel process for preparing optically active trimethyllactic acid and/or its esters by catalytic hydrogenation of trimethylpyruvic acid and/or its esters in the presence of noble metal complex catalysts containing phosphorus ligands.

5 Claims, No Drawings-

OTHER PUBLICATIONS

Tetrahedron: Asymmetry vol. 3, No. 1, pp. 13–16, (month unavailable) 1992, A New Type of Atropisomeric Biphenyl-bisphosphine Ligand, (R)–MOC–BIMOP and Its Use in Efficient Asymmetric Hydrogenation of α–Aminoketone and Itaconic Acid[1], Kiyoshi Yoshikawa, Noako Yamamoto, Masanao Murata, Katsuya Awano. Toshiaki Morimoto, and Kazuo Achiwa.

J. Am. Chem. Soc. (month unavailable) 1993, 115, pp. 10125–10138, Preparation and Use of $C_2$–Symmetric Bis(phospholanes): Production of α–Amino Acid Derivatives via Highly Enantioselective Hydrogenation Reactions, Mark J. Burk, John E. Feaster, William A. Nugent, and Richard L. Harlow.

J. Chem. Soc., Chem. Commun., (month unavailable) 1985, pp. 922–924, Synthesis of Novel Chiral Ruthenium Complexes of 2,2'–Bis(diphenylphosphino)–1,1'–binaphthyl and their Use as Asymmetric Catalysts, Takao Ikariya, Youichi Ishii, Hiroyuki Kawano, Tsuneta Arai, Masahiko Saburi, Sadao Yoshikawa, and Susumu Akutagawa.

J. Am. Chem. Soc. (month unavailable) 1987, 109, pp. 5856–5858, Asymmetric Hydrogenation of β–Keto Carboxylic Esters. A Pratical, Purely Chemical Access to β–Hydroxy Esters in High Enantiomeric Purity, R. Noyori, T. Ohkuma, and M. Kitamura.

Organometallics (month unavailable) 1993, 12, pp. 1467–1470, In Situ Generation of Ruthenium–Chiral Phosphine Complexes and Their Use in Asymmetric Hydrogenation, Thanikavelu Manimaran, Tse–Chong Wu, W. Dirk Klobucar, Charles H. Kolich, and G. Patrick Stahly.

* cited by examiner

PROCESS FOR PREPARING OPTICALLY ACTIVE TRIMETHYLLACTIC ACID AND ITS ESTERS

BACKGROUND OF THE INVENTION

The invention relates to a novel process for preparing optically active trimethyllactic acid and/or esters thereof by catalytic hydrogenation of trimethylpyruvic acid and/or esters thereof.

Optically active trimethyllactic acid or its esters are required, for example, as building blocks for HIV protease inhibitors (*Bioorg. Med. Chem. Lett.*, 1995, 5, 1729–1734). Its synthesis is therefore of particular importance.

A number of synthesis routes are already known. *Biotechnol. Biotech.*, 1986, 8–13, describes, for example, enzymatically reducing trimethylpyruvic acid in an enantioselective manner using an alcohol dehydrogenase. However, the process has the disadvantage that the reaction must be carried out in the presence of a cofactor whose regeneration is complex and expensive.

In addition, both chemical (*Bull. Chem,. Soc. Jpn.*, 1968, 41, 2178–2179) and biological methods are described (*Appl. Environ. Microbio.*, 1983, 45, 884–891) for the racemate resolution of trimethyllactic acid. The disadvantage of these methods is that the maximum yield for the target enantiomer, as is customary in racemate resolutions, is 50%, and the unwanted enantiomer must usually be discarded.

A further method is the diazotization of tert-leucine with subsequent hydrolysis of the diazonium compound with water (*Chem. Ber.*, 1991, 124, 849–859). However, this process requires the very expensive enantiomerically pure tert-leucine and, due to unwanted rearrangement reactions, leads to by-products and is therefore uneconomic.

*J. Org. Chem.*, 1988, 53, 1231–1238 and *J. Org. Chem.*, 1986, 51, 3396–3398 disclose the preparation of enantiomerically pure trimethyllactic esters by reducing trimethylpyruvic esters with chirally modified borane reagents. However, this process has the disadvantage that stoichiometric amounts of the borane reagent, which is expensive and complicated to synthesize, are required.

EP-A 901,997 discloses a process for preparing optically active alcohols by asymmetric hydrogenation of ketones. However, the process is restricted exclusively to aliphatic or aliphatic/aromatic ketones, hydrogenation being carried out in the presence of transition metal complex catalysts, a base, and a diamine. The transition metal complex catalysts contain bisphosphine ligands.

EP-A 643,065 discloses further specific bisphosphines which can be used for asymmetric hydrogenations in the form of their complexes with metals of Group VIII, in particular ruthenium. Suitable substrates mentioned are generally substituted or unsubstituted α- or β-keto esters, α- or β-keto amides, α- or β-amino- or α- or β-hydroxyketones and acetamidocinnamic acid derivatives. The focus of use is the asymmetric hydrogenation of 2-arylpropenoic acids.

In addition, EP-A 654,406 describes ferrocenyldiphosphines as ligands for homogeneous rhodium and iridium catalysts, which are used for the asymmetric hydrogenation of prochiral compounds containing carbon-carbon and carbon-heteroatom double bonds. Examples of such compounds are prochiral olefins, enamines, imines, and ketones.

For the sterically demanding methyl phenylpyruvate, *Tetrahedron: Asymmetry*, 5, 675–690 describes an asymmetric hydrogenation in the presence of various phosphine ligands which, although they predominantly lead to very high yields, at the same time give only unsatisfactory enantiomeric excesses, some of which are in the range of only 27 or 30% ee.

The object of the present invention is thus to provide a novel process which makes possible the enantioselective preparation of optically active trimethyllactic acid and its esters with high yields and does not require the use of expensive reagents.

SUMMARY OF THE INVENTION

The invention relates to a process for preparing optically active trimethyllactic acid and/or esters thereof of formula (I)

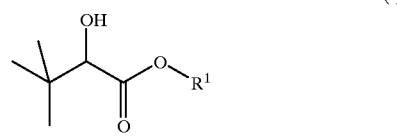

wherein $R^1$ represents hydrogen, alkyl, aryl, aralkyl, or heterocyclyl, comprising enatiomerically hydrogenating trimethylpyruvic acid and/or its esters of formula (II)

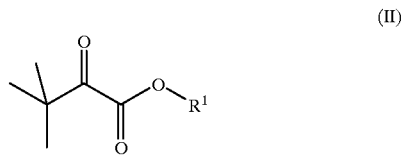

wherein $R^1$ has the meanings specified for formula (I), in the presence of a catalyst comprising one or more noble metal complexes containing optically active bisphosphines as ligands.

DETAILED DESCRIPTION OF THE INVENTION

The inventive process makes possible the enantiomerically pure preparation of trimethyllactic acid and/or its esters of the general formula (I), where the radical $R^1$ represents H, alkyl, aryl, aralkyl, or heterocyclyl. The alkyl radicals in the above-mentioned substituents can in each case be unbranched or branched.

Preferably, the radical $R^1$ represents H, $C_1$–$C_{20}$-alkyl, $C_6$–$C_{14}$-aryl, $C_7$–$C_{15}$-aralkyl, or $C_2$–$C_{12}$-heterocyclyl. Suitable $C_2$–$C_{12}$-heterocyclyl groups can have one or more three- to- seven-membered rings having at least one ring nitrogen, oxygen, and/or sulfur heteroatom in addition to the specified number of ring carbon atoms and are preferably $C_2$–$C_{12}$-heteroaryl groups in which at least one of the rings is aromatic. Particularly preferably, $R^1$ represents H, $C_1$–$C_{10}$-alkyl, $C_6$–$C_{10}$-aryl, $C_7$–$C_{11}$-aralkyl or $C_2$–$C_9$-heteroaryl and, in particular hydrogen, methyl, ethyl, propyl, isopropyl, butyl, isobutyl, sec-butyl, pentyl, neopentyl, isopentyl, phenyl, benzyl, naphthyl, 2-furyl, 3-furyl, 2-pyrrolyl, and 3-pyrrolyl.

The alkyl, aryl, aralkyl, and heteroaryl radicals can, in addition, also be further substituted by Cl, Br, F, I, $C_1$–$C_4$-alkoxy, or $C_1$–$C_4$-alkyl.

In the inventive process, catalysts having the following enantiomerically pure bisphosphines of the general formula (B1) to (B15) can be used, for example:

(1) a bisphosphine of the general formula (B1)

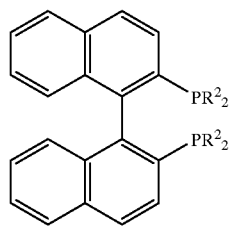

(B1)

where

R² denotes phenyl, 3-methylphenyl, 4-methylphenyl, 3,5-dimethylphenyl, 4-methoxyphenyl, 3,5-dimethyl-4-methoxyphenyl, cyclohexyl, or cyclopentyl, or (2) a bisphosphine of the general formula (B2)

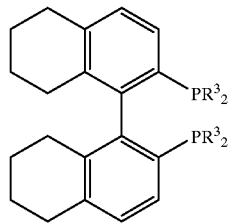

(B2)

where

R³ denotes phenyl, 4-methylphenyl, 3,5-dimethylphenyl, 4-methoxyphenyl, 3,5-dimethyl-4-methoxyphenyl, or cyclohexyl, or (3) a bisphosphine of the general formula (B3)

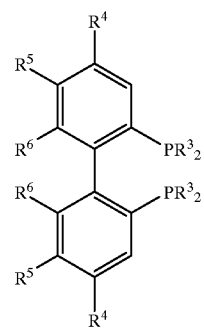

(B3)

where

R³ denotes phenyl, 4-methylphenyl, 3,5-dimethylphenyl, 4-methoxyphenyl, 3,5-dimethyl-4-methoxyphenyl, or cyclohexyl, R⁴ denotes H, methyl, or methoxy, R⁵ denotes H, methyl, methoxy, or chlorine, and R⁶ denotes methyl, methoxy, or trifluoromethyl, or (4) a bisphosphine of the general formula (B4)

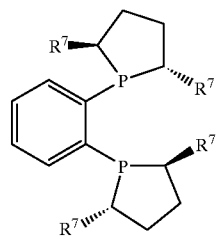

(B4)

where

R⁷ represents methyl, ethyl, propyl, or isopropyl, or (5) 2,3-bis(diphenylphosphino)butane of the formula (B5)

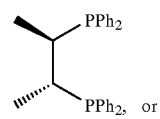

(B5)

(6) 1,2-bis(diphenylphosphino)propane of the formula (B6)

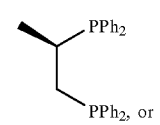

(B6)

(7) 5,6-bis(diphenylphosphino)-2-norbornane of the formula (B7)

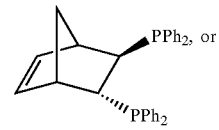

(B7)

(8) 1-substituted 3,4-bis(diphenylphosphino)pyrrolidine of the formula (B8)

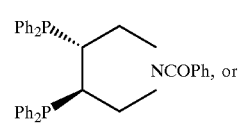

(B8)

(9) 2,4-bis(diphenylphosphino)pentane of the formula (B9)

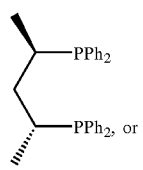

(B9)

(10) 2,3-O-isopropylidene-2,3-dihydroxy-1,4-bis(diphenylphosphino)-butane of the formula (B10)

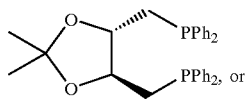
(B10)

(11) 1,2-bis-[(o-methoxyphenyl)phenylphosphino]ethane of the formula (B11)

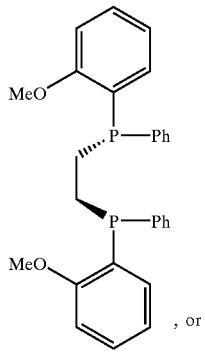
(B11)

(12) 1-[1',2-bis(diphenylphosphino)ferrocenyl]ethanol of the formula (B12)

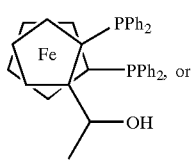
(B12)

(13) 1-tert-butoxycarbonyl-4-diphenylphosphino-2-diphenylphosphino-methyl-pyrrolidine of the formula (B13)

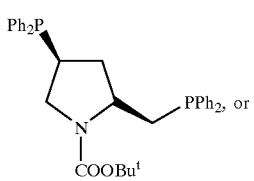
(B13)

(14) a bisphosphine of the general formula (B14)

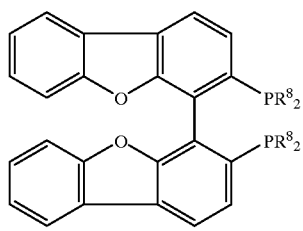
(B14)

where
R$^8$ denotes phenyl, cyclohexyl, 4-methylphenyl, 4-methoxyphenyl, 3,5-dimethylphenyl, 3,5-dimethyl-4-methoxyphenyl, 4-tert-butyl, or 3,5-di-tert-butyl, or

(15) a ferrocenyldiphosphine of the general formula (B15)

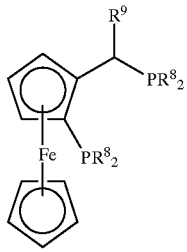
(B15)

where
R$^8$ has the meaning specified for formula (B14) and
R$^9$ denotes $C_1$–$C_8$-alkyl, phenyl, or phenyl monosubstituted to trisubstituted by $C_1$–$C_4$-alkoxy.

Suitable bisphosphines of the above-mentioned formula (B1) are.
2,2μ-bis(diphenylphosphino)-1,1μ-binaphthyl,
2,2μ-bis(di-4-tolylphosphino)-1,1μ-binaphthyl
  described in *J. Org. Chem.*, 1986, 51, 629.

Suitable bisphosphines of the above-mentioned formula (B3) are
(5,5'-dichloro-6,6'-dimethoxybiphenyl-2,2'-diyl)-bisdiphenylphosphine
  described in EP-A 749,973
(4,4',6,6'-tetramethyl-5,5'-dimethoxybiphenyl-2,2'-diyl)-bis(diphenylphosphine)
(4,4',6,6'-tetramethyl-5,5'-dimethoxybiphenyl-2,2'-diyl)-bis(di-p-methoxyphenylphosphine)
  described in *Chem. Pharm. Bull.*, 1991, 39, 1085
(4,4',6,6'-tetratrifluoromethylbiphenyl-2,2'-diyl)-bis(diphenylphosphine)
(4,6-ditrifluoromethyl-4',6'-dimethyl-5'-methoxybiphenyl-2,2'-diyl)-bis(diphenyl-phosphine)
  described in Synlett 1991, 827
(2-dicyclohexyl-2'-diphenylphosphino-4,4',6,6'-tetramethyl-5,5'-dimethoxybiphenyl-2,2'-diyl)-bis(diphenylphosphine)
  described in *Tetrahedron: Asymmetry*, 1992, 3, 13
(6,6'-dimethyl-2,2'-biphenylene)-bis(diphenylphosphine)
(4,4',6,6'-tetramethyl-2,2'-biphenylene)-bis(diphenylphosphine)
(3,3',6,6'-tetramethyl-2,2'-biphenylene)-bis(diphenylphosphine)
(4,4'-difluoro-6,6'-dimethyl-2,2'-biphenylene)-bis(diphenylphosphine)
(4,4'-bis(dimethylamino)-6,6'-dimethyl-2,2'-biphenylene)-bis(diphenyl-phosphine)
(6,6'-dimethyl-2,2'-biphenylene)-bis(di-p-tolylphosphine)
(6,6'-dimethyl-2,2'-biphenylene)-bis (di-o-tolylphosphine)
(6,6'-dimethyl-2,2'-biphenylene)-bis(di-m-fluorophenylphosphine)
1,11-bis(diphenylphosphino)-5,7-dihydrodibenzo[c,e]oxepine
  described in JP-B 4-15796 (where "B" denotes: examined Japanese patent application)
(6,6'-dimethoxybiphenyl-2,2'-diyl)-bis(diphenylphosphine)
(5,5',6,6'-tetramethoxybiphenyl-2,2'-diyl)-bis(diphenylphosphine)

(6,6'-dimethoxybiphenyl-2,2'-diyl)-bis(di-p-tolylphosphine) and (4,4',5,5',6,6'-hexamethoxybiphenyl-2,2'-diyl)-bis(diphenylphosphine)

described in JP-A 3-5492.

Suitable bisphosphines of the formula (B4) are:
1,2-bis(2,5-dimethylphosphorano)benzene
1,2-bis(2,5-diethylphosphorano)benzene
1,2-bis(2,5-dipropylphosphorano)benzene and
1,2-bis(2,5-diisopropylphosphorano)benzene described in *J. Am. Chem. Soc.,* 1993, 115, 10125.

Preferred noble metal complex catalysts in the inventive process are particularly those based on ruthenium, rhodium, and iridium. Particularly preferably, ruthenium complex catalysts are used.

Suitable complexes are, for example, the following ruthenium complexes of optically active bisphosphines defined by the general formulas (III) to (X), without being restricted thereto:

| | |
|---|---|
| $Ru_2Cl_4B_2(S)$ | (III) |
| $[Ru\ Hal\ Q\ B]^+\ Y^-$ | (IV) |
| $Ru\ B_n\ OOCR^{10}OOCR^{11}$ | (V) |
| $[Ru\ H_x\ B_n]^{m+}\ Y^{m-}$ | (VI) |
| $[Ru\ Hal\ (PR^{12}{}_2R^{13})B]^{(2+)}Hal^-{}_2$ | (VII) |
| $[Ru\ H\ Hal\ B_2]$ | (VIII) |
| $[B\ Ru\ (acac)_2]$ | (IX) |
| $[B\ Ru\ Y_2]$ | (X) | where acac denotes acetylacetonate,

B represents a bisphosphine of the general formulas (B1) to (B15),

Hal represents halogen, in particular chlorine, bromine, or iodine, $R^{10}$ and $R^{11}$ are identical or different and represent $C_1$–$C_9$-alkyl (preferably $C_1$–$C_4$-alkyl) which is optionally substituted by halogen (particularly fluorine, chlorine, or bromine), phenyl which is optionally substituted by $C_1$–$C_4$-alkyl, or an α-aminoalkyl acid having preferably up to 4 carbon atoms, or $R^{10}$ and $R^{11}$ together form an alkylidene group having up to 4 carbon atoms, $R^{12}$ and $R^{13}$ are identical or different and represent optionally substituted phenyl (preferably substituted by $C_1$–$C_4$-alkyl or halogen), Y represents halogen, $ClO_4$, $BF_4$, or $PF_6$, Q represents an unsubstituted or substituted benzene ring, preferably p-cymene, S represents a tertiary amine, preferably triethylamine, tri-n-butyl-amine, or pyridine, n and m are identical or different and are 1 or 2, and x represents 0 or 1, with the proviso that in formula (VI) n represents 1 and m represents 2 when x is 0, and n represents 2 and m represents 1 when x is 1.

The complexes of the general formulae (III) to (IX) can be prepared by known methods.

The complexes of the formulae (III) and (VIII) may be prepared, for example, in a manner similar to that according to the processes described in EP-A 174,057 or in *J. Chem Soc. Chem. Comm.,* 922 (1985).

The complexes of the general formula (IV) are given by, for example, reacting known ruthenium complexes $[RuHal_2Q]_2$ with bisphosphines of the general formula (B1) in inert organic solvents, for example as described in EP-A 366,390 or EP-A 749,973.

Complexes of the general formula (V) where n is 1 can be obtained, for example, by processes which are specified in EP-A 245,959, by reacting complexes of the general formula (III) with the corresponding carboxylic acids.

Complexes of the general formula (V) where n is 2 or n is 1 and $R^{10}$ and $R^{11}$ are $CF_3$ can be prepared by processes specified in EP-A 272,787.

The complexes of the general formula (VI) can be prepared in a similar manner to the process according to EP-A 256,634.

The complexes of the general formula (VII) can be prepared in a similar manner to the process according to EP-A 470,756.

Complexes of the general formula (IX) can be prepared in a similar manner to the processes specified in *Organometallics,* 1993, 1467.

The complexes of formula (X) can be prepared in a similar manner to the processes specified in *J. Am. Chem. Soc.,* 1987, 109, 5856–5858 or in *Tetrahedron: Asymmetry,* 5, 1994, 675–690.

Complexes based on rhodium or iridium can also be prepared by known methods by, for example, reacting, in a suitable, inert organic or aqueous solvent, the corresponding bisphosphine with a compound which can release rhodium or iridium.

Rhodium-releasing compounds that can be used, are, for example organic rhodium complexes with ethylene or propylene or with bisolefins such as 1,5-cyclooctadiene, 1,5-hexadiene, bicyclo[2,2,1]hepta-2,5-diene or with other dienes that readily form soluble complexes with rhodium. Preferred rhodium-releasing compounds are, for example, dichloro-bis-(1,5-cyclooctadiene)dirhodium, dichloro-bis (norbornadiene)dirhodium, bis-(1,5-cyclococtadiene) rhodium tetrafluoroborate, or bis(cyclooctadiene)rhodium perchlorate. An iridium-releasing compound which may be mentioned is, for example, dichloro-bis-(1,5-cyclooctadiene)diiridium.

When the inventive process is carried out, these catalyst complexes can be prepared first and, if appropriate, isolated and then added to a solution of the starting materials of the general formula (II). Alternatively, however, they can also be prepared in situ, that is to say already in the presence of the starting materials of the general formula (II).

In the preparation of the catalyst complexes, the ratio of metals to bisphosphines of the general formula (B1) to (B15) is expediently in the range 0.5 to 2 mol, preferably in the range 0.9 to 1.1 mol of ruthenium per mole of bisphosphine ligand. The ratio of metal in the complexes to the compounds of the formula (II) is customarily in the range 1:10 to $1:10^6$, preferably in the range 1:30 to $1:10^5$.

The enantioselective hydrogenation can be performed in a suitable organic solvent which is inert under the reaction conditions. Suitable solvents of this type, are, for example, lower alcohols having 1 to 6 carbon atoms, or mixtures of such alcohols with halogenated hydrocarbons, such as methylene chloride or chloroform, or with ethers or cyclic ethers such as diethyl ether, tetrahydrofuran, or dioxane, or with ketones such as acetone, methyl ethyl ketone, or methyl isobutyl ketone. Compounds that are also suitable as mixing partners are aliphatic hydrocarbons, such as hexane and heptane, cycloaliphatic hydrocarbons, such as cyclohexane and methylcyclohexane, or aromatic hydrocarbons, such as toluene and benzene. The mixing partners can, if appropriate, also be used in pure form.

Compounds of the general formula (II) are expediently enantioselectively hydrogenated in the presence of optically active bisphosphine catalysts at a temperature in the range 0 to 150° C., preferably in the range 15 to 100° C.

The pressure is in the range 1 to 250 bar hydrogen, preferably in the range 5 to 200 bar, and particular preference is given to a hydrogen pressure in the range 20 to 180 bar.

The inventive process is distinguished by a very good yield and a simultaneously high enantioselectivity. The use of cofactor—as in the case of the enzymatic reduction using an alcohol dehydrogenase—is not necessary. Also, the use of borane reagents which are expensive and complicated to synthesize is not necessary. It is surprising that the optically active bisphosphine ligands which are already known for other asymmetric hydrogenations also lead to an excellent enantioselectivity in the case of the trimethylpyruvic acid (esters) used here, which are highly demanding sterically. Enantiomeric excesses of 40% ee or more are achieved. Preferably, enantiomeric excesses $\geq 90\%$ ee are achieved, and in particular $\geq 95\%$ ee.

EXAMPLES

The enantiomers of (5,5'-dichloro-6,6'-dimethoxy-biphenyl-2,2'-diyl)-bis(diphenylphosphine) were prepared in accordance with Examples 3 to 7 in EP-A 749,973, a counterpart of U.S. Pat. Nos. 5,710,339 and 5,801,261, which are incorporated herein by reference.

Trimethylpyruvic acid is commercially available. Its esters can be produced according to known processes from trimethylpyruvic acid by acid esterification. Enantiomeric excesses, unless stated otherwise, were determined by means of gas chromatography (GC).

Example 1

15 ml of distilled acetone was placed in a flask under argon (5.0), evacuated with stirring, and aerated with argon. This process was repeated three times. Then, with stirring, and in an argon countercurrent, 61.5 mg of (R)-(+)-2,2$\mu$-bis(diphenylphosphino)-1,1$\mu$-binaphthyl (supplier: Acros) and 30.8 mg of bis-(2-methylallyl)cycloocta-1,5-diene ruthenium (III) complex (supplier: Acros) were dissolved in the acetone. To the resultant suspension were added 0.84 ml of hydrogen bromide (w(HBr)=48%) and the mixture was twice evacuated with stirring and aerated with argon. The mixture was then further stirred for 0.5 h under argon. An orange-red solution was formed.

In a further flask 0.52 g of methyl trimethylpyruvate and 50 ml of distilled methanol were introduced under argon. This solution was three times evacuated with stirring and aerated with argon. The catalyst solution was then forced with argon from the first flask through a hollow needle into the second flask. The resultant yellow turbid solution was then forced by argon into a 0.3 liter V$_4$A stainless steel autoclave, which had been purged five times in advance with 100 bar nitrogen (5.0).

The autoclave was heated to 50° C. with stirring (1,000 rpm). At 50° C. the system was pressurized to 150 bar with hydrogen and hydrogenated for 24 hours under these conditions.

The autoclave was then cooled to room temperature, depressurized, and purged with nitrogen.

According to GC, the yield of methyl trimethyllacetate was quantitative and the enantiomeric excess of the R enantiomer was 97.8%.

Example 2

15 ml of distilled acetone were placed in a flask under argon (5.0), evacuated with stirring, and aerated with argon. This process was repeated three times. Then, with stirring and in an argon countercurrent, 49.9 mg of (4S,5S)-(+)-4,5-bis(diphenylphosphinomethyl)-2,3-dimethyl-1,3-dioxolane (supplier: Aldrich) and 30.8 mg of bis-(2-methylallyl)cycloocta-1,5-diene ruthenium (III) complex (supplier: Acros) were dissolved in the acetone. To the resultant suspension were added 0.84 ml of hydrogen bromide (w(HBr)=48%) and the mixture was twice evacuated with stirring and aerated with argon. The mixture was then further stirred for 0.5 h under argon. An orange-red solution was formed.

In a further flask, 0.52 g of methyl trimethylpyruvate and 50 ml of distilled methanol were introduced under argon. This solution was three times evacuated with stirring and aerated with argon. The catalyst solution was then forced from the first flask by argon through a hollow needle into the second flask. The resultant yellow turbid solution was then forced by argon into a 0.3 liter V$_4$A stainless steel autoclave which had been flushed in advance five times with 100 bar nitrogen (5.0).

The autoclave was heated to 50° C. with stirring (1,000 rpm). At 50° C. the system was pressurized with 150 bar hydrogen and hydrogenation was carried out under these conditions for 24 hours. The autoclave was then cooled to room temperature, depressurized, and purged with nitrogen.

According to GC, the yield of methyl trimethyllactate was 37% and the enantiomeric excess of the R enantiomer was 44%.

Example 3

15 ml of distilled acetone were placed in a flask under argon (5.0), evacuated with stirring, and aerated with argon. This process was repeated three times. Then, with stirring, and in an argon countercurrent, 42.6 mg of (2S,3S)-(−)-bis(diphenylphosphino)butane (supplier: Aldrich) and 30.8 mg of bis-(2-methylallyl)cycloocta-1,5-diene ruthenium (III) complex (supplier: Acros) were dissolved in the acetone. To the resultant suspension were added 0.84 ml of hydrogen bromide (w(HBr)=48%) and the mixture was twice evacuated with stirring and aerated with argon. The mixture was then further stirred for 0.5 h under argon. An orange-red solution was formed.

In a further flask, 0.52 g of methyl trimethylpyruvate and 50 ml of distilled methanol were introduced under argon. This solution was three times evacuated with stirring and aerated with argon. The catalyst solution was then forced from the first flask by argon through a hollow needle into the second flask. The resultant yellow turbid solution was then forced by argon into a 0.3 liter V$_4$A stainless steel autoclave which had been purged in advance five times with 100 bar nitrogen (5.0).

The autoclave was heated to 50° C. with stirring (1,000 rpm). At 50° C. the system was pressurized to 150 bar with hydrogen and hydrogenation was carried out for 24 hours under these conditions. The autoclave was then cooled to room temperature, depressurized, and purged with nitrogen.

According to GC the yield of methyl trimethyllactate was 16% and the enantiomeric excess of the R enantiomer was 53.4%.

Example 4

15 ml of distilled acetone were placed in a flask under argon (5.0), evacuated with stirring, and aerated with argon. This process was repeated three times. Then, with stirring, and in an argon countercurrent, 65.1 mg of (+)-(5,5'-dichloro-6,6'-dimethoxybiphenyl-2,2'-diyl)-bis(diphenylphosphine) and 30.8 mg of bis-(2-methylallyl)cycloocta-1,5-diene ruthenium (III) complex (supplier: Acros) were dissolved in the acetone. To the resultant suspension were added 0.84 ml of hydrogen bromide (w(HBr)=48%) and the mixture was twice evacuated with stirring and aerated with argon. The mixture was then further stirred for 0.5 h under argon. An orange-red solution was formed.

In a further flask, 0.52 g of methyl trimethylpyruvate and 50 ml of distilled methanol were introduced under argon. This solution was three times evacuated with stirring and aerated with argon. The catalyst solution was then forced from the first flask by argon through a hollow needle into the second flask. The resultant yellow turbid solution was then forced by argon into a 0.3 liter $V_4A$ stainless steel autoclave, which had been purged in advance five times with 100 bar nitrogen (5.0).

The autoclave was heated to 50° C. with stirring (1,000 rpm). At 50° C. the system was pressurized to 150 bar with hydrogen and hydrogenation was carried out for 24 hours under these conditions. The autoclave was then cooled to room temperature, depressurized, and purged with nitrogen.

According to GC the yield of methyl trimethyllactate was 97.5% and the enantiomeric excess of the R enantiomer was >98%.

Example 5

15 ml of distilled acetone were placed in a flask under argon (5.0), evacuated with stirring, and aerated with argon. This process was repeated three times. Then, with stirring, and in an argon countercurrent, 65.1 mg of (+)-(5,5'-dichloro-6,6'-dimethoxybiphenyl-2,2'-diyl)-bis(diphenylphosphine) and 30.8 mg of bis-(2-methylallyl)cycloocta-1,5-diene ruthenium (III) complex (supplier: Acros) were dissolved in the acetone. To the resultant suspension were added 0.84 ml of hydrogen bromide (w(HBr)=48%) and the mixture was twice evacuated with stirring and aerated with argon. The mixture was then further stirred for 0.5 h under argon. An orange-red solution was formed.

In a further flask, 5.2 g of methyl trimethylpyruvate and 50 ml of distilled methanol were introduced under argon. This solution was three times evacuated with stirring and aerated with argon. The catalyst solution was then forced from the first flask by argon through a hollow needle into the second flask. The resultant yellow turbid solution was then forced by argon into a 0.3 liter $V_4A$ stainless steel autoclave, which had been purged in advance five times with 100 bar nitrogen (5.0).

The autoclave was heated to 50° C. with stirring (1,000 rpm). At 50° C. the system was pressurized to 150 bar with hydrogen and hydrogenation was carried out for 24 hours under these conditions. The autoclave was then cooled to room temperature, depressurized, and purged with nitrogen. The hydrogenation solution was then freed from the solvent and distilled.

The isolated yield was 3 g (58% of theory). According to GC the content of methyl (R)-trimethyllactate was >99% with an enantiomeric excess >98% ee.

Example 6

15 ml of distilled acetone were placed in a flask under argon (5.0), evacuated with stirring, and aerated with argon. This process was repeated three times. Then, with stirring, and in an argon countercurrent, 13 mg of (+)-(5,5'-dichloro-6,6'-dimethoxybiphenyl-2,2'-diyl)-bis(diphenylphosphine) and 6.2 mg of bis-(2-methylallyl)cycloocta-1,5-diene ruthenium (III) complex (supplier: Acros) were dissolved in the acetone. To the resultant suspension were added 0.17 ml of hydrogen bromide (w(HBr)=48%) and the mixture was twice evacuated with stirring and aerated with argon. The mixture was then further stirred for 0.5 h under argon. An orange-red solution was formed.

In a further flask, 10.4 g of methyl trimethylpyruvate and 50 ml of distilled methanol were introduced under argon. This solution was three times evacuated with stirring and aerated with argon. The catalyst solution was then forced from the first flask by argon through a hollow needle into the second flask. The resultant yellow turbid solution was then forced by argon into a 0.3 liter $V_4A$ stainless steel autoclave, which had been purged in advance five times with 100 bar nitrogen (5.0).

The autoclave was heated to 50° C. with stirring (1,000 rpm). At 50° C. the system was pressurized to 150 bar with hydrogen and hydrogenation was carried out for 24 hours under these conditions. The autoclave was then cooled to room temperature, depressurized, and purged with nitrogen. The hydrogenation solution was then freed from the solvent under reduced pressure.

The isolated yield was 9.6 g (92% of theory). According to GC the content of methyl (R)-trimethyllactate was >99% with an enantiomeric excess of 98% ee.

Example 7

0.52 g of methyl trimethylpyruvate and 65 ml of methanol were placed in a flask under argon (5.0), evacuated with stirring, and aerated with argon. This process was repeated three times. To the solution were added, in an argon countercurrent, 113.6 mg of [Ru(+)-(5,5'-dichloro-6,6'-dimethoxybiphenyl-2,2'-diyl)-bis(diphenylphosphine) Cym I] I and the mixture was three times evacuated with stirring and aerated with argon. The solution was then forced by argon into a 0.3 liter $V_4A$ stainless steel autoclave which had been purged in advance five times with 100 bar nitrogen (5.0).

The autoclave was heated to 50° C. with stirring (1,000 rpm). At 50° C. the system was pressurized to 150 bar with hydrogen and hydrogenation was carried out under these conditions for 24 hours. The autoclave was then cooled to room temperature, depressurized, and purged with nitrogen.

The hydrogenation solution was concentrated on a rotary evaporator at 50° C. and 200 to 20 mbar. The conversion was, according to GC, quantitative to the methyl (R)-trimethyllactate with an enantiomeric excess of 95.8% ee.

Example 8

0.52 g of methyl trimethylpyruvate and 65 ml of methanol were placed in a flask under argon (5.0), evacuated with stirring, and aerated with argon. This process was repeated three times. To the solution were added, in an argon countercurrent, 79.9 mg of [Ru(+)-(5,5'-dichloro-6,6'-dimethoxybiphenyl-2,2'-diyl)-bis(diphenylphosphine) $OAc_2$] and the system was three times evacuated with stirring and aerated with argon. The solution was then forced by argon into a 0.3 liter $V_4A$ stainless steel autoclave which had been purged in advance three times with 100 bar nitrogen (5.0).

The autoclave was heated to 50° C. with stirring (1,000 rpm). At 50° C., the system was pressurized to 150 bar with hydrogen and hydrogenation was carried out for 24 hours under these conditions. The autoclave was then cooled to room temperature, depressurized, and purged with nitrogen. The hydrogenation solution was concentrated on a rotary evaporator at 50° C. and 200 to 20 mbar.

The conversion to methyl (R)-trimethyllactate was quantitative according to GC with an enantiomeric excess of 41.3% ee.

Example 9

0.76 g of trimethylpyruvic acid (distilled) and 65 ml of methanol were placed in a flask under argon (5.0), evacuated with stirring, and aerated with argon. This process was repeated three times. To the solution were added, in an argon countercurrent, 113.6 mg of [Ru(+)-(5,5'-dichloro-6,6'-dimethoxybiphenyl-2,2'-diyl)-bis(diphenylphosphine) Cym I] I and the system was three times evacuated with stirring and aerated with argon. The solution was then forced by argon into a 0.3 liter $V_4A$ stainless steel autoclave which had been purged in advance five times with 100 bar nitrogen (5.0).

The autoclave was heated to 50° C. with stirring (1,000 rpm). At 50° C. the system was pressurized to 150 bar with hydrogen and hydrogenation was carried out for 24 hours under these conditions. The autoclave was then cooled to room temperature, depressurized, and purged with nitrogen. The hydrogenation solution was concentrated on a rotary evaporator at 50° C. and 200 to 20 mbar.

The yield according to GC was approximately 84% to give the (R)-trimethyllactic acid with an enantiomeric excess of 78% ee.

What is claimed is:

1. A process for preparing optically active trimethyllactic acid and/or esters thereof having formula (I)

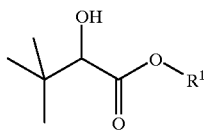

(I)

wherein $R^1$ represents hydrogen, alkyl, aryl, aralkyl, or heterocyclyl, comprising enatiomerically hydrogenating trimethylpyruvic acid and/or esters thereof having formula (II)

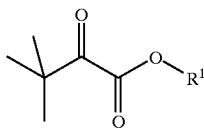

(II)

wherein $R^1$ has the meanings specified for formula (I), in the presence of a catalyst comprising one or more noble metal complexes containing optically active bisphosphines as ligands selected from the group consisting of (1) a bisphosphine of formula (B1)

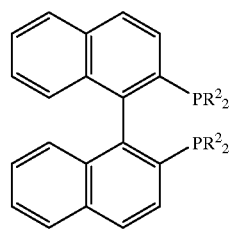

(B1)

where
$R^2$ denotes phenyl, 3-methylphenyl, 4-methylphenyl, 3,5-dimethylphenyl, 4-methoxyphenyl, 3,5-dimethyl-4-methoxyphenyl, cyclohexyl, or cyclopentyl, or (2) a bisphosphine of formula (B2)

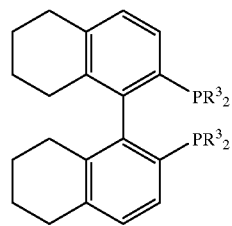

(B2)

where
$R^3$ denotes phenyl, 4-methylphenyl, 3,5-dimethylphenyl, 4-methoxyphenyl, 3,5-dimethyl-4-methoxyphenyl, or cyclohexyl, or (3) a bisphosphine of formula (B3)

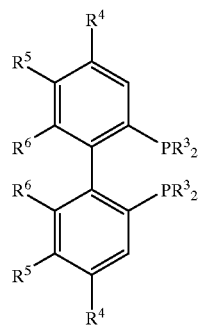

(B3)

where
$R^3$ denotes phenyl, 4-methylphenyl, 3,5-dimethylphenyl, 4-methoxyphenyl, 3,5-dimethyl-4-methoxyphenyl, or cyclohexyl,
$R^4$ denotes H, methyl, or methoxy,
$R^5$ denotes H, methyl, methoxy, or chlorine, and
$R^6$ denotes methyl, methoxy, or trifluoromethyl, or (4) a bisphosphine of formula (B4)

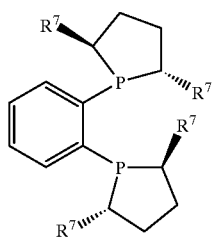
(B4)

where
R[7] represents methyl, ethyl, propyl, or isopropyl, or (5) 2,3-bis(diphenylphosphino)butane of formula (B5)

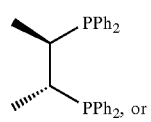
(B5)

(6) 1,2-bis(diphenylphosphino)propane of formula (B6)

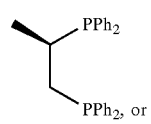
(B6)

(7) 5,6-bis(diphenylphosphino)-2-norbornane of formula (B7)

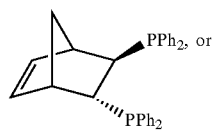
(B7)

(8) 1-substituted 3,4-bis(diphenylphosphino) pyrrolidine of formula (B8)

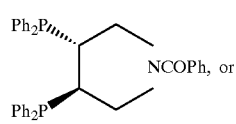
(B8)

(9) 2,4-bis(diphenylphosphino)pentane of formula (B9)

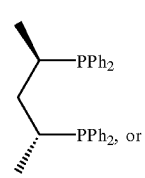
(B9)

(10) 2,3-O-isopropylidene-2,3-dihydroxy-1,4-bis(diphenylphosphino)butane of formula (B10)

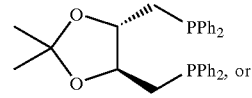
(B10)

(11) 1,2-bis-[(o-methoxyphenyl)phenylphosphino]ethane of formula (B11)

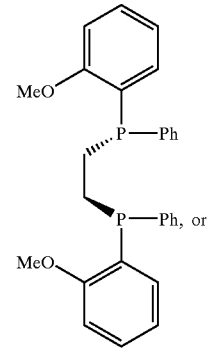
(B11)

(12) 1-[1',2-bis(diphenylphosphino)ferrocenyl]ethanol of formula (B12)

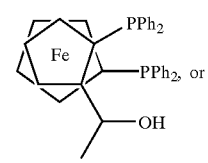
(B12)

(13) 1-tert-butoxycarbonyl-4-diphenylphosphino-2-diphenylphosphinomethyl-pyrrolidine of formula (B13)

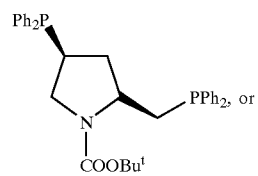
(B13)

(14) a bisphosphine of formula (B14)

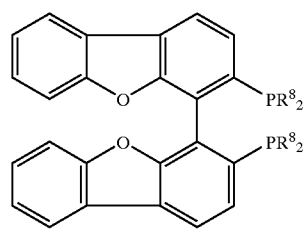
(B14)

where
R⁸ denotes phenyl, cyclohexyl, 4-methylphenyl, 4-methoxyphenyl, 3,5-dimethylphenyl, 3,5-dimethyl-4-methoxyphenyl, 4-tert-butyl, or 3,5-di-tert-butyl, or

(15) a ferrocenyldiphosphine of formula (B15)

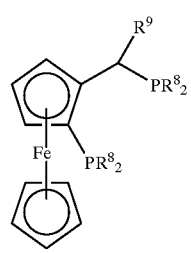

(B15)

where
R⁸ denotes phenyl, cyclohexyl, 4-methylphenyl, 4-methoxyphenyl, 3,5-dimethylphenyl, 3,5-dimethyl-4-methoxyphenyl, 4-tert-butyl, or 3,5-di-tert-butyl, and
R⁹ denotes $C_1$–$C_8$-alkyl, phenyl, or phenyl monosubstituted to trisubstituted by $C_1$–$C_4$-alkoxy.

2. A process according to claim 1 wherein the bisphosphine of formula (B1) is 2,2μ-bis(diphenylphosphino)-1,1μ-binaphthyl or 2,2μ-bis(di-4-tolylphosphino)-1,1μ-binaphthyl.

3. A process according to claim 1 wherein the bisphosphine of formula (B3) is selected from the group consisting of (5,5'-dichloro-6,6'-dimethoxybiphenyl-2,2'-diyl)-bisdiphenylphosphine,
(4,4',6,6'-tetramethyl-5,5'-dimethoxybiphenyl-2,2'-diyl)-bis(diphenyl-phosphine),
(4,4',6,6'-tetramethyl-5,5'-dimethoxybiphenyl-2,2'-diyl)-bis(di-p-methoxy-phenylphosphine), phosphine),
(4,4',6,6'-tetramethyl-5,5'-dimethoxybiphenyl-2,2'-diyl)-bis(di-p-methoxy-phenylphosphine),
(4,4',6,6'-tetratrifluoromethylbiphenyl-2,2'-diyl)-bis(diphenylphosphine)
(4,6-ditrifluoromethyl-4',6'-dimethyl-5'-methoxybiphenyl-2,2'-diyl)-bis-(diphenyl-phosphine),
(2-dicyclohexyl-2'-diphenylphosphino-4,4',6,6'-tetramethyl-5,5'-dimethoxybiphenyl-2,2'-diyl)-bis(diphenylphosphine),
(6,6'-dimethyl-2,2'-biphenylene)-bis(diphenylphosphine),
(4,4',6,6'-tetramethyl-2,2'-biphenylene)-bis(diphenylphosphine),
(3,3',6,6'-tetramethyl-2,2'-biphenylene)-bis(diphenylphosphine),
(4,4'-difluoro-6,6'-dimethyl-2,2'-biphenylene)-bis(diphenylphosphine),
(4,4'-bis(dimethylamino)-6,6'-dimethyl-2,2'-biphenylene)-bis(diphenylphosphine),
(6,6'-dimethyl-2,2'-biphenylene)-bis(di-p-tolylphosphine),
(6,6'-dimethyl-2,2'-biphenylene)-bis (di-o-tolylphosphine),
(6,6'-dimethyl-2,2'-biphenylene)-bis(di-m-fluorophenylphosphine),
1,11-bis(diphenylphosphino)-5,7-dihydrodibenzo[c,e]oxepine,
(6,6'-dimethoxybiphenyl-2,2'-diyl)-bis(diphenylphosphine),
(5,5',6,6'-tetramethoxybiphenyl-2,2'-diyl)-bis(diphenylphosphine),
(6,6'-dimethoxybiphenyl-2,2'-diyl)-bis(di-p-tolylphosphine), and
(4,4',5,5',6,6'-hexamethoxybiphenyl-2,2'-diyl)-bis(diphenylphosphine).

4. A process according to claim 1 wherein the bisphosphine of formula (B4) is selected from the group consisting of 1,2-bis(2,5-dimethylphosphorano)benzene,
1,2-bis(2,5-diethylphosphorano)benzene,
1,2-bis(2,5-dipropylphosphorano)benzene, and
1,2-bis(2,5-diisopropylphosphorano)benzene.

5. A process according to claim 1 wherein the noble metal complex catalyst is a ruthenium complex of an optically active bisphosphine selected from compounds having the formulas

| | |
|---|---|
| $Ru_2Cl_4B_2(S)$ | (III), |
| $[Ru\ Hal\ Q\ B]^+Y^-$ | (IV), |
| $Ru\ B_n\ OOCR^{10}OOCR^{11}$ | (V), |
| $[Ru\ H_xB_n]^{m+}Y^{m-}$ | (VI), |
| $[Ru\ Hal\ (PR^{12}_2R^{13})B]^{(2+)}Hal^-_2$ | (VII), |
| $[Ru\ H\ Hal\ B_2]$ | (VIII), |
| $[B\ Ru\ (acac)_2]$ | (IX), and |
| $[B\ Ru\ Y_2]$ | (X), | where acac denotes acetylacetonate,

Hal represents halogen, $R^{10}$ and $R^{11}$ are identical or different and represent $C_1$–$C_9$-alkyl which is optionally substituted by halogen, phenyl which is optionally substituted by $C_1$–$C_4$-alkyl, or an α-aminoalkyl acid, or $R^{10}$ and $R^{11}$ together form an alkylidene group having up to 4 carbon atoms, $R^{12}$ and $R^{13}$ are identical or different and represent optionally substituted phenyl, Y represents halogen, $ClO_4$, $BF_4$, or $PF_6$, Q represents an unsubstituted or substituted benzene ring, S represents a tertiary amine, n and m are identical or different and are 1 or 2, x represents 0 or 1, and B represents (1) a bisphosphine of formula (B1)

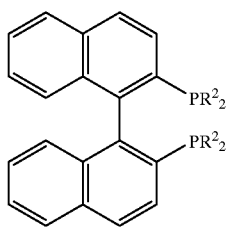
(B1)

where
R² denotes phenyl, 3-methylphenyl, 4-methylphenyl, 3,5-dimethylphenyl, 4-methoxyphenyl, 3,5-dimethyl-4-methoxyphenyl, cyclohexyl, or cyclopentyl, or (2) a bisphosphine of formula (B2)

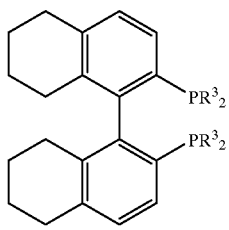
(B2)

where
R³ denotes phenyl, 4-methylphenyl, 3,5-dimethylphenyl, 4-methoxyphenyl, 3,5-dimethyl-4-methoxyphenyl, or cyclohexyl, or (3) a bisphosphine of formula (B3)

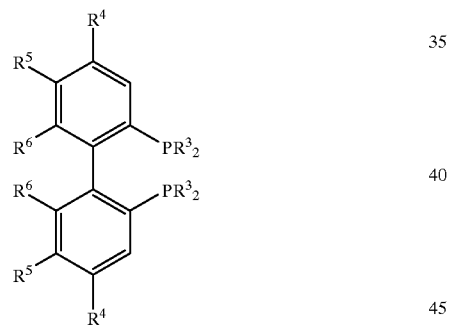
(B3)

where
R³ denotes phenyl, 4-methylphenyl, 3,5-dimethylphenyl, 4-methoxyphenyl, 3,5-dimethyl-4-methoxyphenyl, or cyclohexyl,
R⁴ denotes H, methyl, or methoxy,
R⁵ denotes H, methyl, methoxy, or chlorine, and
R⁶ denotes methyl, methoxy, or trifluoromethyl, or (4) a bisphosphine of formula (B4)

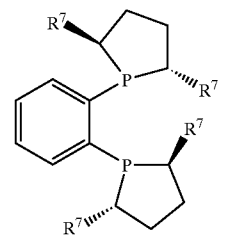
(B4)

where
R⁷ represents methyl, ethyl, propyl, or isopropyl, or (5) 2,3-bis(diphenylphosphino)butane of formula (B5)

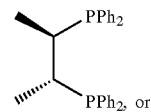
(B5)

(6) 1,2-bis(diphenylphosphino)propane of formula (B6)

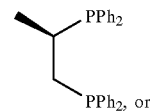
(B6)

(7) 5,6-bis(diphenylphosphino)-2-norbornane of formula (B7)

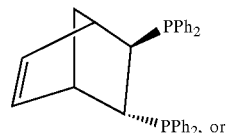
(B7)

(8) 1-substituted 3,4-bis(diphenylphosphino) pyrrolidine of formula (B8)

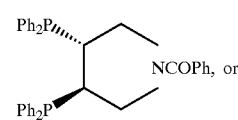
(B8)

(9) 2,4-bis(diphenylphosphino)pentane of formula (B9)

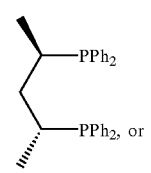
(B9)

(10) 2,3-O-isopropylidene-2,3-dihydroxy-1,4-bis(diphenylphosphino)butane of formula (B10)

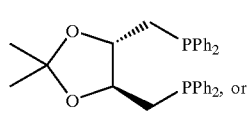
(B10)

(11) 1,2-bis-[(o-methoxyphenyl)phenylphosphino] ethane of formula (B11)

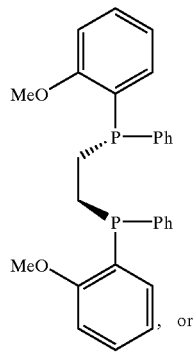
(B11)

, or

(12) 1-[1',2-bis(diphenylphosphino)ferrocenyl]ethanol of formula (B12)

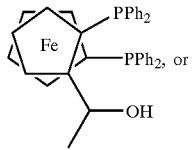
(B12)

(13) 1-tert-butoxycarbonyl-4-diphenylphosphino-2-diphenylphosphino-methyl-pyrrolidine of formula (B13)

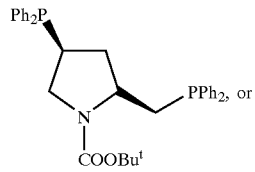
(B13)

(14) a bisphosphine of formula (B14)

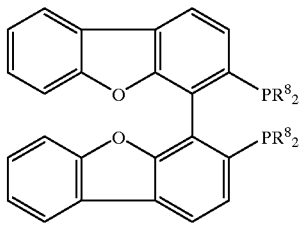
(B14)

where
$R^8$ denotes phenyl, cyclohexyl, 4-methylphenyl, 4-methoxyphenyl, 3,5-dimethylphenyl, 3,5-dimethyl-4-methoxyphenyl, 4-tert-butyl, or 3,5-di-tert-butyl, or

(15) a ferrocenyldiphosphine of formula (B15)

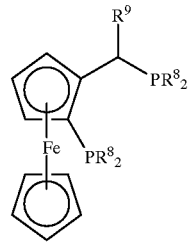
(B15)

where
$R^8$ denotes phenyl, cyclohexyl, 4-methylphenyl, 4-methoxyphenyl, 3,5-dimethylphenyl, 3,5-dimethyl-4-methoxyphenyl, 4-tert-butyl, or 3,5-di-tert-butyl, and
$R^9$ denotes $C_1$–$C_8$-alkyl, phenyl, or phenyl mono-substituted to trisubstituted by $C_1$–$C_4$-alkoxy, with the proviso that in formula (VI) n represents 1 and m represents 2 when x is 0, and n represents 2 and m represents 1 when x is 1.

* * * * *